United States Patent

Dysarz

[11] Patent Number: 6,102,894
[45] Date of Patent: Aug. 15, 2000

[54] MODULAR RETRACTABLE SPRING NEEDLE CANNULA BLOOD COLLECTION DEVICE

[76] Inventor: Edward D. Dysarz, 18 Front St., Rockport, Tex. 78382

[21] Appl. No.: 09/307,846

[22] Filed: May 10, 1999

[51] Int. Cl.⁷ ................................................. A61M 5/00
[52] U.S. Cl. ...................... 604/110; 604/195; 604/198; 128/763
[58] Field of Search .................... 604/110, 195, 604/198, 263, 192, 187; 128/763–766, 919

[56] References Cited

U.S. PATENT DOCUMENTS

| | | | |
|---|---|---|---|
| 4,850,977 | 7/1989 | Bayless | 604/198 |
| 4,887,998 | 12/1989 | Martin et al. | 604/198 |
| 4,946,446 | 8/1990 | Vadher | 604/263 X |
| 5,423,758 | 6/1995 | Shaw | 604/195 |
| 5,769,826 | 6/1998 | Johnson et al. | 604/195 |

*Primary Examiner*—John D. Yasko

[57] ABSTRACT

A modular retractable spring cannula blood collection device that is comprised of a needle cannula with a rigid first end and a biased spring formed at the second end. The second end of the needle cannula that is formed into a biased spring needle cannula is contained in an elongated hollow tube with a first end and a second end wherein the first end has a cannula support tunnel and a hub is formed at the second end. The second end of the biased spring needle cannula is fixed to the second end of the elongated hollow tube and a latching means is fixed to the spring needle cannula and wherein the latching means is fixed to a latch release near the first end of the elongated hollow tube thereby supporting the first end of the spring needle cannula and thereby further restraining the biased spring needle cannula within the elongated hollow tube. The first end of the spring needle cannula extends past the cannula support tunnel wherein the first end of the needle cannula is injected into a body and further withdraws blood from the body wherein the blood flows through the spring needle cannula, and into a vacutainer fixed to the hub of the elongated hollow tube and wherein the blood further flows into a vial in the vacutainer wherein the vial is suitably filled with blood and removed from the vacutainer.

The latch release means is activated thereby releasing the latch means, further allowing the biased spring needle cannula to withdraw the first end of the spring needle cannula into the elongated hollow tube thereby preventing an accidental prick or injury.

11 Claims, 6 Drawing Sheets

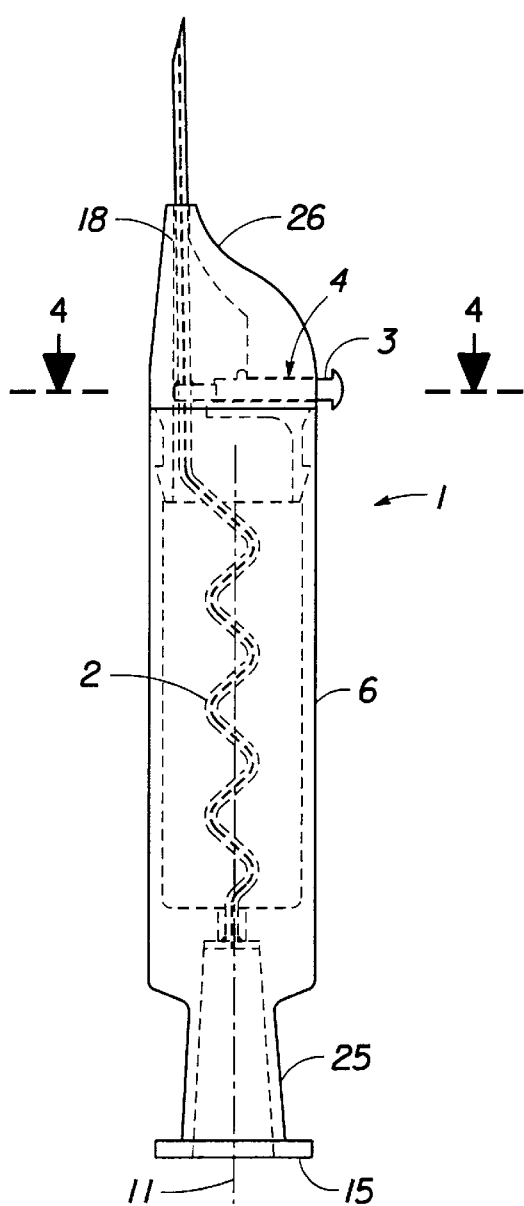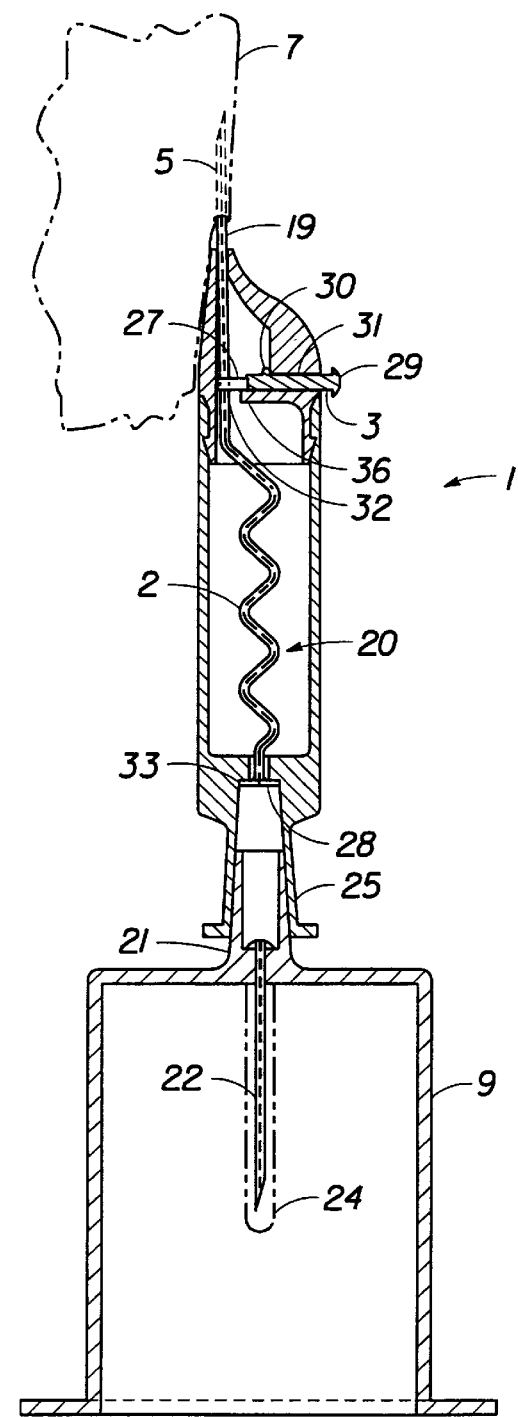
Fig. 2
Fig. 3

MODULAR RETRACTABLE SPRING NEEDLE CANNULA BLOOD COLLECTION DEVICE

BACKGROUND OF INVENTION

There are several types of safety blood sampling designs available today. One such design is shown in a patent issued to Jagger et al. on Jun. 3, 1986 U.S. Pat. No. 4,592,744. This safety blood sampling device however that requires two (2) hands to operate or to cover the needle cannula.

Blood samples are also taken with syringes and there are also many safety syringes available. Some of these designs have a sleeve or sheath that will cover the needle after it has been used. Some typical designs with sleeves or sheaths are Z. M. Roehr et al. U.S. Pat. No. 3,008,570, Z. M. Roehr U.S. Pat. No. 3,107,785, Bartner et al. U.S. Pat. No. 3,895,633, G. K. Burke U.S. Pat. No. 3,306,291, Gyure et al. U.S. Pat. No. 4,300,678, Winstead Hall U.S. Pat. No. 4,356,822, Sampson U.S. Pat. No. 4,425,120, Larson U.S. Pat. No. 4,639,249, Harbaugh U.S. Pat. No. 4,655,751, Strauss U.S. Pat. No. 4,664,654, Braginetz U.S. Pat. No. 466,435, Spencer U.S. Pat. No. 4,702,738, Milorad U.S. Pat. No. 4,702,739, Spencer U.S. Pat. No. 4,801,295, Poncy U.S. Pat. No. 4,816,022, and Hughes U.S. Pat. No. 4,840,619.

Other designs have a retractable needle such as Weltman U.S. Pat. No. 3,306,290, and Dent U.S. Pat. No. 4,392,859. These designs do not have a means whereby the needle is extended from the syringe and held in place in a positive and rigid position in order to first inject the needle prior to drawing blood or injecting the medication. Still other designs have methods of bending the needle to render it harmless after the medication has been injected. Most of these designs have one major purpose and that is to prevent the spread of infectious diseases such as aids, hepatitis, or other diseases from accidental injection with a contaminated needle into others after the needle of the blood sampling device or syringe has been inserted into a patient with the above mentioned disease. These various designs all work well to a degree, but they all fall short of their intended purpose during the act of covering the needle, or removing the needle, which requires two hands.

All of these designs require at least two hands to operate. The use of two hands to cover the contaminated needle is most unsatisfactory in that during the act of placing a second hand on the blood sampling device or syringe, the person holding the blood sampling device or syringe in one hand may be bumped and accidentally inject the needle into their other hand before it can grasp the blood sampling device or syringe. Other accidental jabbings or injections can happen in an ambulance where just as a person tries to grasp the contaminated blood sampling device or syringe, the ambulance can hit a bump in the road causing the person holding the blood sampling device or syringe to accidentally stick another person or themselves with the contaminated needle. The need has developed for a blood sampling device or syringe that will cover the contaminated needle with the use of only one hand.

None of these safety blood sampling devices or safety syringe designs are modularized wherein they can be used for blood sampling with a vacutainer assembly.

SUMMARY

It is the object of this invention to provide a blood sampling device wherein the needle of the blood sampling device is retracted into the barrel of the blood sampling device and thereby protect others from an accidental pricking after it has been used; the needle cannula can be retracted into the barrel with the use of only one hand and that one hand being the hand that was used to inject the needle cannula into a patient.

It is still another object of the present invention to further prevent the accidental release of the needle cannula after the needle cannula is in the barrel of the blood sampling device.

It is still yet another object of the present invention to provide a blood sampling device wherein the needle cannula is sloped for ease of skin penetration.

It is still yet even another object of the present invention to provide a safety blood sampling device that is modularized.

And still yet even another object of the present invention is to render the blood sampling device useless after the needle cannula is retracted into the barrel of the blood sampling device to prevent the accidental reuse of the contaminated device.

The foregoing and other objects and advantages are attained by a safety blood sampling device, with a hollow sloping cannula guide, a spring needle cannula, a hub that is attached to a vacutainer wherein when said blood sampling device is used to inject a needle cannula into a vein in the body or part of the body in order to withdraw blood for testing purposes, the latch means is released and the spring needle cannula withdraws the rigid needle cannula into the elongated hollow tube thereby rendering the rigid needle cannula harmless to prevent the accidental pricking of others.

The features of the present invention can be best understood together with further objects and advantages by reference to the following descriptions taken in conjunction with accompanying drawing, wherein like numerals indicate like parts.

BRIEF DESCRIPTION OF THE DRAWINGS

FIG. 2 is an elevation view of the device of the preferred embodiment.

FIG. 3 is an enlarged section elevation of the device of the preferred embodiment.

DETAILED DESCRIPTION OF THE PREFERRED EMBODIMENT

Figure 1:
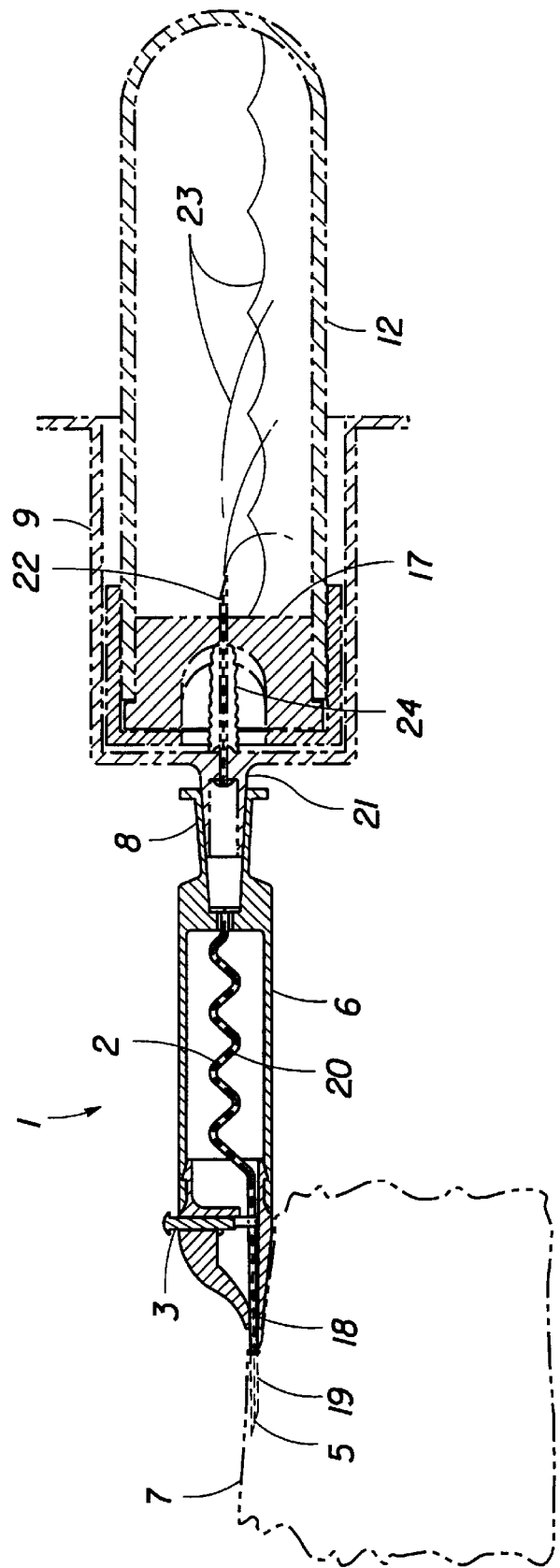
FIG. 1 is a section elevation view of the device of preferred embodiment in use.

Referring to FIG. 1 there is shown a section elevation of the modular retractable spring needle cannula blood collection device 1. The device 1 is comprised of a aggregate needle cannula 20 with a first end and a second end wherein the first end is a rigid needle cannula 19 and the second end is a biased spring needle cannula 2. The first end of the rigid needle cannula 19 has a cannula point 5 that has been injected into a body 7 wherein blood or other fluid flows from said body 7 through the rigid needle cannula 19 and through the biased spring needle cannula 20, through the hub 8, through the vacutainer foundation 21, through the vacutainer needle cannula 22 and into the blood collection vial 12. The blood 23 is shown flowing into the blood collection vial 12.

The depressor shaft 3 is shown near the first end of the elongated hollow tube 6. The rigid needle cannula 19 is shown disposed in the cannula tunnel 18 and further extending from the cannula support tunnel 18 into the body 7.

The vacutainer needle cannula 22 is shown suitably penetrating the vial cap 17 that is made out of a soft material such as rubber. The vacutainer needle cannula cover 24 is shown pushed back by the vial cap 17 when the vial cap 17 was thrust onto the vacutainer needle cannula 22.

Referring to FIG. 2 there is shown an enlarged elevation of the device 1 without the vacutainer fixed to the device 1.

The first end of the aggregate needle cannula 20 is shown extending from the cannula support tunnel 18 that is on the first end of the elongated hollow tube cap 26. The biased spring needle cannula 2 is shown on the inside of the elongated hollow tube 6. The hub 25 is shown with a first end and a second end. The first end of the hub 25 is shown fixed to second end of the elongated hollow tube 6 and the second end of the hub 25 is shown fixed to the first end of the hub flange 15. The hub flange 15 is shown with a first end and a second end. The cannula support tunnel 18 is shown eccentric to the center line 11 of the elongated hollow tube 6 to allow the rigid needle cannula 19 to be easily injected into the body 7.

The depressor shaft 3 is shown extending out of the second end of the elongated hollow tube cap 26. The depressor shaft 3 is part of the cannula release means 4 that will be shown more clearly in FIGS. 3, 4, 5, and 6.

Referring to FIG. 3 there is shown an enlarged section elevation of the device 1 suitably fixed to the vacutainer 9.

The first section of the aggregate needle cannula 20 is the rigid needle cannula 19 with a cannula point 5 at the first end and the cannula cam 27 near the second end. The biased spring needle cannula 2 is shown with the cannula cam 27 near the first end and the cannula flange 28 near the second end. The biased spring needle cannula 2 is at the second end of the aggregate needle cannula 20.

The depressor shaft 3 is shown with a button cap 29 at the first end and a button stop 30 near the second end. The button stop 30 prevents the depressor shaft 3 from falling out of or being withdrawn from the depressor button passage 31. The second end of the depressor shaft 3 is essentially near the third end of the cannula cam 27.

The cannula cam 27 has a first end, a second end, a third end, a first side, and a second side. The first side of the cannula cam 27 is near the rigid needle cannula 19, the second side of the cannula cam 27 is near the biased spring needle cannula 2, the first end of the cannula cam 27 is near the second end of the depressor shaft 3, and the second end of the cannula cam 27 is near the aggregate needle cannula 20. A cannula hole 32 is formed near the second end of the cannula cam 27 that extends from the first side of the cannula cam 27 to the second side of the cannula cam 27 and the biased spring needle cannula 2 is suitably disposed in the cannula hole 32. The biased spring needle cannula 2 is also suitably fixed to the cannula cam 27 with adhesive, welding or some other suitable means.

The cannula cam 27 is also shown caught on the cam stop 36. The biased spring needle cannula 2 is pulling on the cannula cam 27 and the cannula cam 27 is restrained by the cam stop 36.

The second end of the biased spring needle cannula 2 has a cannula flange 28, suitably fixed to the biased spring needle cannula 2 by welding, adhesive or some other suitable means. The cannula flange 28 is held in the first end of the hub 25 by a hub ridge 33. The hub ridge 33 is formed near the first end of the hub 25. A fluid tight or gas tight connection may be formed between the hub ridge 33 and the cannula flange 28 by adhesive, welding or a gasket by design choice.

The vacutainer hub foundation 21 is shown suitably held on the inside surface of the hub 25 by friction or adhesive by design choice, a threaded connection could also be used by design choice. The vacutainer needle cannula 22 is shown projecting from the vacutainer hub foundation 21. The vacutainer needle cannula 22 is also shown covered with a soft sheath 34 to keep the vacutainer needle cannula 22 clean.

Figure 4:
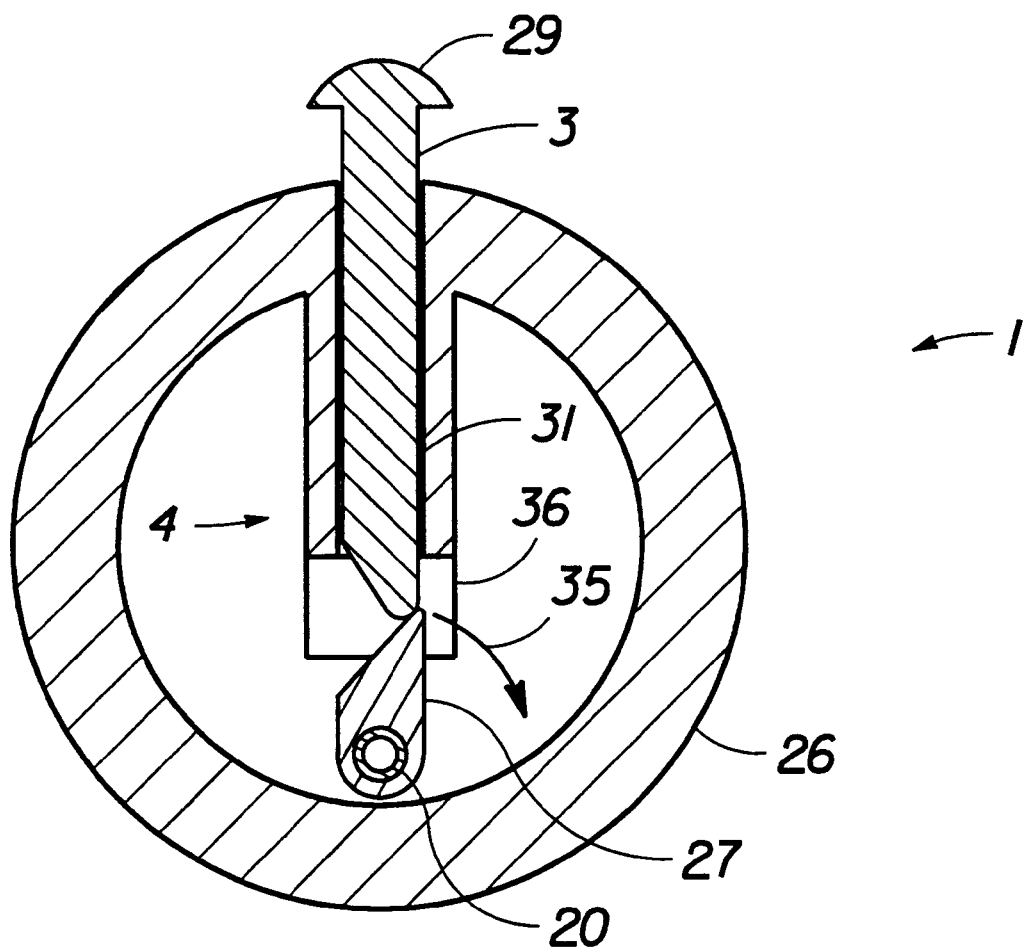
FIG. 4 is a section elevation view as taken through FIG. 2.

Referring to FIG. 4 there is shown a section elevation of the release means 4 of the device 1 as taken through FIG. 2.

The depressor shaft 3 is shown suitably held in the depressor button passage 31. The button cap 29 is shown at the first end of the depressor shaft 3 and the second end of the depressor shaft 3 is shown engaged with the first end of the cannula cam 27. The cannula cam 27 has a first end, a second end, a first side, a second side, and a hole formed between the first end and the second end wherein the hole extends from the first side to the second side of the cannula cam 27 and the aggregate needle cannula 20 is disposed in said hole and fixed to said hole. The aggregate needle cannula 20 is shown disposed and suitably fixed to the cannula cam 27 and is further resisting any rotational 35 forces. The cannula cam 27 is shown further hooked on the cam stop 36 and thereby preventing the first end aggregate needle cannula 20 from being withdrawn into the elongated hollow tube cap 26 or the elongated hollow tube.

Figure 5:
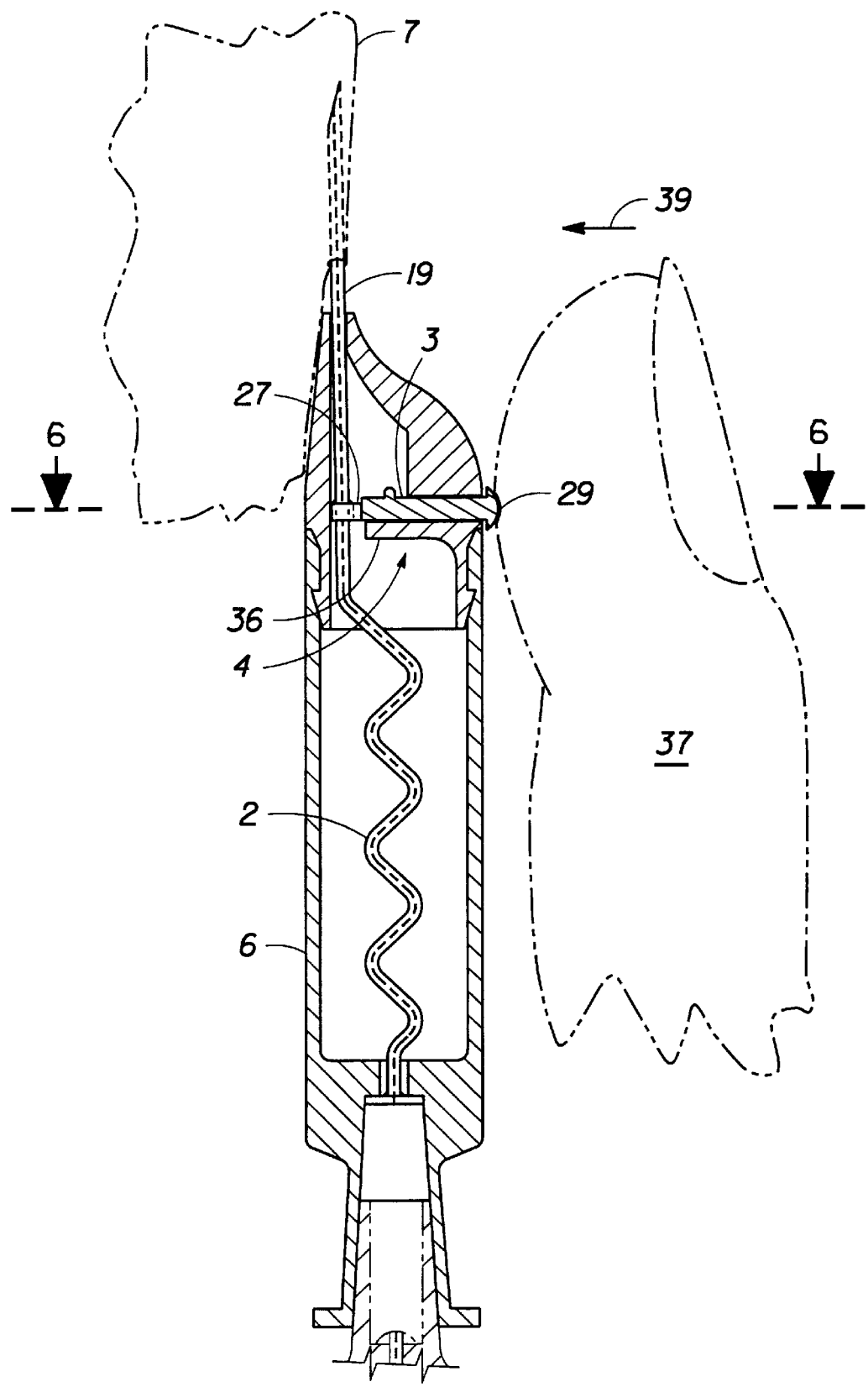
FIG. 5 is another section elevation showing the latch means being released.

Referring to FIG. 5 there is shown a section elevation view of the finger 37 depressing the button cap 28 that in turn depresses the depressor shaft 3 in a depressed direction 39, and thereby releases the cannula release means 4.

As the depressor shaft 3 is depressed the second end of the depressor shaft 3 engages the cannula cam 27 and rotates the cannula cam 27 away from the cam stop 36 (as seen more clearly in FIG. 6) thus releasing the cannula cam 27 from the cam stop 36 and thus further releasing the rigid needle cannula 19 and further allowing the biased spring needle cannula 2 to pull the rigid needle cannula 19 into the elongated hollow tube 6. As the biased spring needle cannula 2 withdraws into the second end of the elongated hollow tube 6, the first end of the rigid needle cannula 19 is withdrawn from the body 7.

Figure 6:
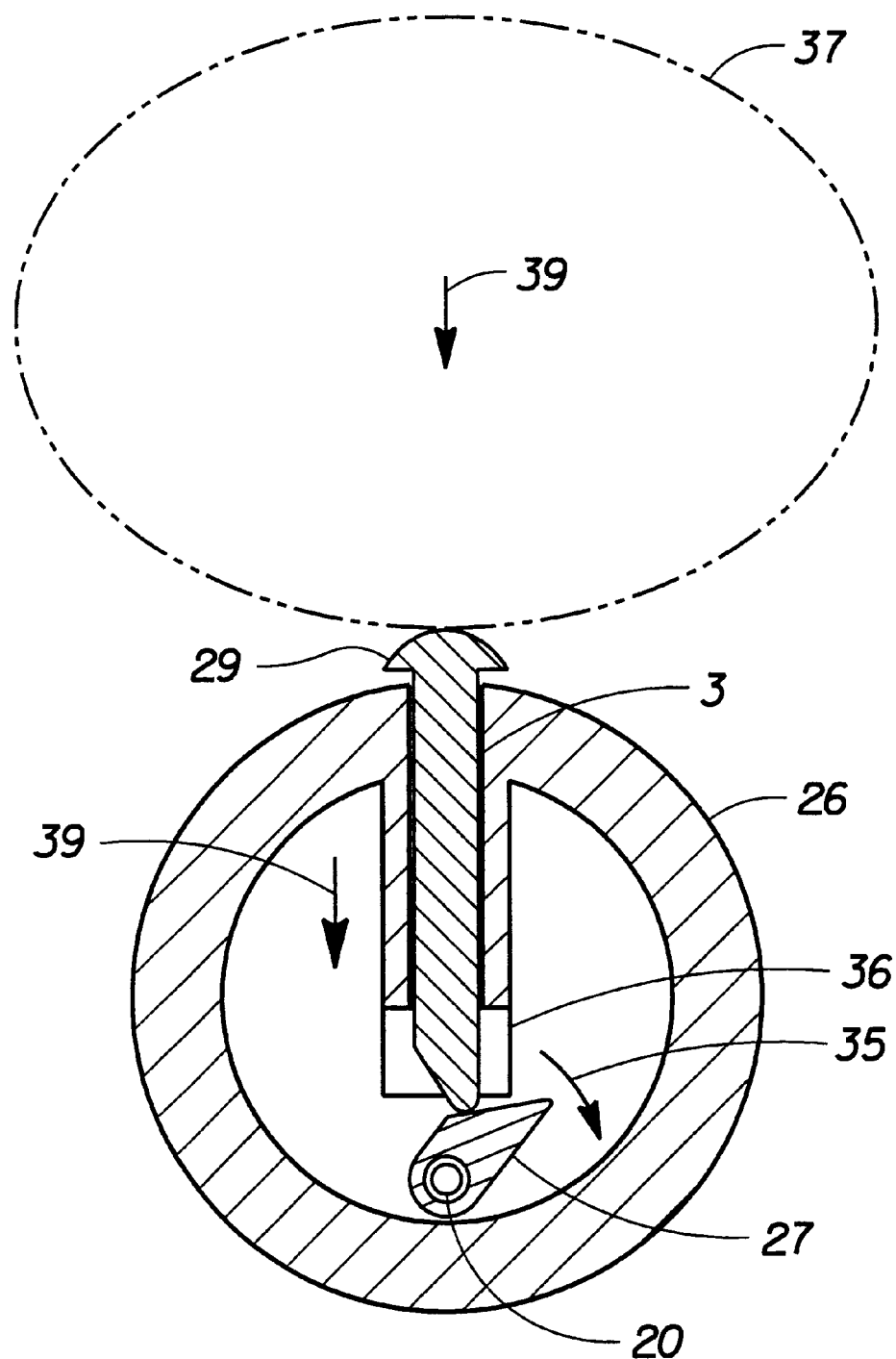
FIG. 6 is a section elevation view as taken through FIG. 5.

Referring to FIG. 6 there is shown a section elevation view of the device 1 as the cannula release means 4 is activated to release the biased spring needle cannula 2.

A finger 37 or thumb presses the button cap 29 on the first end of the depressor shaft 3 in a depressed direction 39. The second end of the depressor shaft 3 engages the first end of the cannula cam 27 and rotates 35 the cannula cam 27 about the aggregate needle cannula 20 thereby causing said second side of said cannula cam to disegage the cam stop 36 thereby allowing the biased spring needle cannula at the second end of the aggregate needle cannula 20 to withdraw the rigid needle cannula of the aggregate needle cannula 2 into the elongated hollow tube cap 26 or into the elongated hollow tube.

A finger 37 is shown depressing the button cap 39. The button cap 39 is shown depressing the first end of the depressor shaft 3 in a depressed direction 39. The second end of the depressor shaft 3 is shown pressing the first end of the cannula cam 27 and causing the cannula cam 27 to rotate 35 about the aggregate needle cannula 20 that is disposed in the cannula hole and suitably fixed to said cannula cam 27 with adhesive or by welding or some other suitable means by design choice.

As the second end of the depressor shaft 3 depresses the cannula cam 27 and further causes the cannula cam to rotate 35 about the aggregate needle cannula 20; the first end of the cannula cam 27 is rotated away from the cam stop 36 which will free the cannula cam 27 from the cam stop 36 and allow the biased spring needle cannula to pull the rigid needle cannula and cannula point into the inside of the elongated hollow tube cap 26 and the elongated hollow tube.

Figure 7:
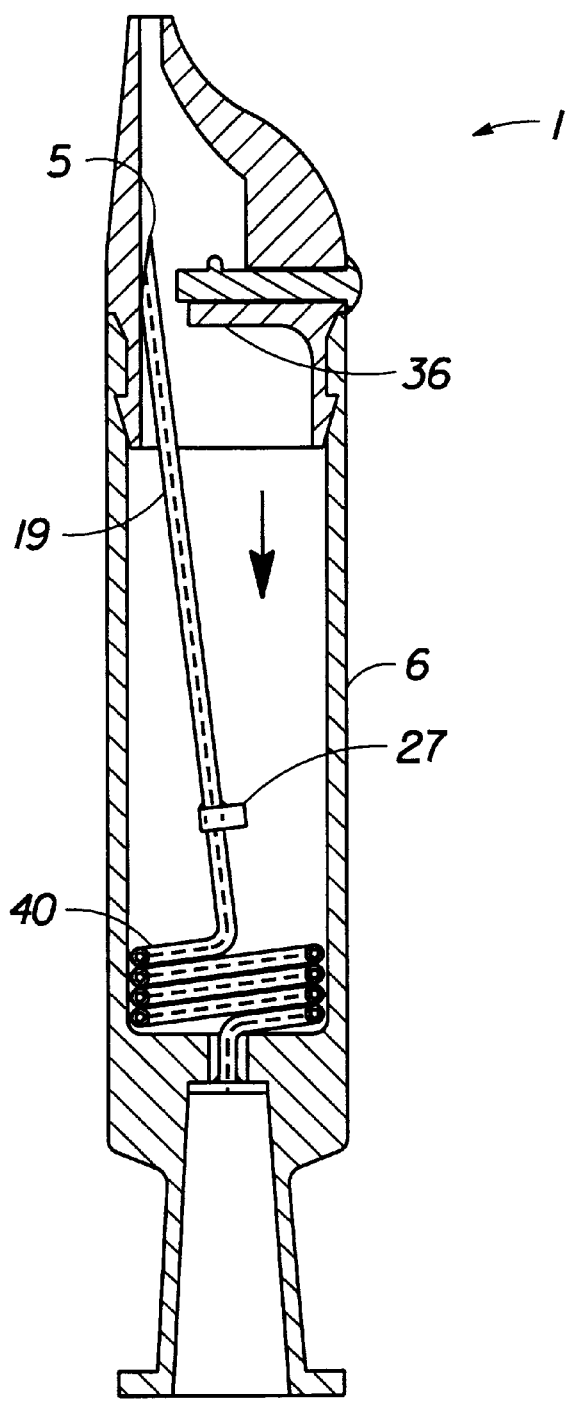
FIG. 7 is a section elevation view of the spring needle cannula withdrawn into the elongated hollow tube.

Referring to FIG. 7 there is shown a section elevation of the device 1 with the rigid needle cannula 19 and cannula point 5, safely contained on the inside of the elongated hollow tube 6.

The cannula cam 27 has been released from the cam stop 36 thereby releasing the biased spring needle cannula 2 and thereby allowing the biased spring needle cannula 2 to withdraw the cannula point 5 into the inside of the elongated hollow tube 6 and the elongated hollow tube 26 wherein the cannula point 5 cannot prick or otherwise injure or prick anyone to spread a disease nor can the rigid needle cannula 19 be reused.

The biased spring needle cannula 2 is no longer biased but shown formed into a coil 40 where it will further prevent the rigid needle cannula 19 from falling out of the elongated hollow tube 6 or from being pulled out of the elongated hollow tube 6.

Although the system described in detail supra has been found to be most satisfactory, many variations are possible. For example, the device could be made out of glass, it could be square or rectangular in section, the device could have a threaded connection or a leur lock at the hub, the device could be a permanent part of the vacutainer and the vacutainer needle cannula.

Although the invention has been described, with reference to the preferred embodiment, it will be understood by those skilled in the art, that additions, modifications, substitutions, deletions and the other changes not specifically described, may be made in the embodiment herein, it should be understood that the details herein are to be interpreted as illustrative and are not in a limiting sense.

What is claimed as invention is:

1. A modular retractable spring needle cannula blood collection device that can be attached and removed from a vacutainer and a blood collection vial, for inserting said needle cannula into a body and transferring blood or other fluid from said body through said device and said vacutainer and into said vial comprising:

an elongated hollow tube having a first end, a second end, an inside surface and an outside surface wherein said elongated hollow tube has a center;

an elongated hollow tube cap with a first end and a second end, an inner surface and an outer surface and wherein said elongated hollow tube cap has a cannula support tunnel formed in said first end of said elongated hollow tube cap and wherein said second end of said elongated hollow tube cap is fixed to said first end of said elongated hollow tube and wherein a depressor button passage is formed near said second end of said elongated hollow tube cap and wherein said depressor button passage extends from said outer surface to said inner surface of said elongated hollow cap;

a hub with a first end and a second end, an inside surface and an outside surface wherein said first end of said hub is fixed to said second end of said elongated hollow tube;

a aggregate needle cannula with a first end, a second end, an inside surface and an outside surface wherein said first end of said aggregate needle cannula is formed into a rigid needle cannula with a first end and a second end and wherein a cannula point is formed at said first end of said rigid needle cannula and wherein said second end of said aggregate needle cannula is formed into a biased spring needle cannula with a first end and a second end and wherein said first end of said biased spring is fixed to said second end of said rigid needle cannula and said second end of said biased spring needle cannula is fixed to said inside surface of said second end of said elongated hollow tube;

a cannula cam, with a first end, a second end, a first side and a second side wherein a hole is formed near said second end of said cannula cam and said hole extends from said first side to said second side of said cannula cam and wherein said rigid needle cannula is disposed in said hole formed in said cannula cam and said rigid needle cannula is fixed to said cannula cam with welding or adhesive;

a cam stop formed on said second end of said elongated hollow tube cap wherein said cam stop has a first end and a second end and wherein said second end of said cam stop extends past said first end of said cannula cam and prevents said cannula cam from being pulled into said elongated hollow tube by said biased spring formed on said biased spring needle cannula;

a depressor shaft with a first end and a second end and wherein a button cap is formed on the first end of said depressor shaft and a stop button is formed near the second end of said depressor shaft and said depressor shaft is disposed in said depressor button passage wherein said second end of said depressor shaft is near said first end of said cannula cam wherein said first end of said rigid needle cannula is inserted into a body and blood or other fluid further flows from said body in said cannula formed in said rigid needle and said spring needle cannula and said blood or said other fluid through said hub into said vacutainer and into said vial wherein when sufficient blood or other fluid is in said vial or other vials, said first end of said biased spring needle cannula is removed from said body and said button cap is pressed with a finger or a thumb or another object further pressing said second end of said depressor shaft into said cannula cam thereby rotating said cannula cam out of the way out of said second end of said cam stop, thus releasing said cannula cam from said cannula cam stop thereby allowing said second end of said biased spring needle cannula to contract and to pull said rigid needle cannula and said cannula point into said elongated hollow tube and said elongated hollow tube cap thereby rendering said rigid needle cannula and said cannula point harmless wherein said cannula point may not prick or injure a person.

2. The modular retractable spring needle blood collection device of claim 1 wherein said support tunnel is eccentric to said center of said elongated hollow tube.

3. The modular retractable spring needle cannula blood collection device of claim 1 wherein said support tunnel is formed at an angle to said center of said elongated hollow tube.

4. The modular retractable spring needle cannula blood collection device of claim 1 wherein a cannula flange is formed on said second end of the biased spring needle cannula and said cannula flange is fixed to a hub ridge formed near said first end of said hub.

5. The modular retractable spring needle cannula blood collection device of claim 1 wherein said biased spring needle cannula is formed out of metal.

6. The modular retractable spring needle cannula blood collection device of claim 1 wherein said biased spring needle cannula is formed out of plastic.

7. The modular retractable spring needle cannula blood collection device of claim 1 wherein said biased spring needle cannula is in constant tension with said cannula cam until said cannula cam is rotated off of said cam stop.

8. The modular retractable spring needle cannula blood collection device of claim 1 wherein said hub can be fixed to a slip tip or a threaded tip of a vacutainer.

9. The modular retractable spring needle cannula blood collection device of claim 1 wherein said device can be placed on a syringe.

10. The modular retractable spring needle cannula blood collection device of claim 1 wherein said biased spring needle cannula will form a coil when released and essentially all tension is relieved.

11. The modular retractable spring needle cannula blood collection device of claim 1 wherein said cannula cam will absorb any back thrust as said rigid needle cannula is inserted into said body.

* * * * *